US006072045A

United States Patent [19]

Chappell et al.

[11] Patent Number: 6,072,045

[45] Date of Patent: Jun. 6, 2000

[54] CHIMERIC ISOPRENOID SYNTHASES AND USES THEREOF

[75] Inventors: Joseph Chappell; Kyoungwhan Back, both of Lexington, Ky.

[73] Assignee: Board of Trustees of the University of Kentucky, Lexington, Ky.

[21] Appl. No.: 09/134,699

[22] Filed: Aug. 14, 1998

Related U.S. Application Data

[63] Continuation of application No. 08/631,341, Apr. 12, 1996, Pat. No. 5,824,774.

[51] Int. Cl.[7] .......... C07H 21/02

[52] U.S. Cl. .......... 536/23.1; 536/23.4; 435/69.1; 435/71.1; 435/69.7

[58] Field of Search .......... 536/23.1, 23.4; 435/69.1, 71.1, 69.7

[56] References Cited

PUBLICATIONS

Cane et al. "Partial Purification and Characterization of Pentalenene Synthase," *Arch. Biochem. Biophys.* 254:421–429 (1987).

Cane et al., "Pentalenene Synthase. Purification, Molecular Cloning, Sequencing, and High–Level Expression in *Escherichia coli* of a Terpenoid Cyclase from Streptomyces UC 5319," *Biochemistry* 33:5846–5857 (1994).

Chappell et al., "Accumulation of Capsidiol in Tobacco Cell Cultures Treated with Fungal Elicitor," *Phytochemistry* 26:2259–2260 (1987).

Chappell, "Biochemistry and Molecular Biology of the Isoprenoid Biosynthetic Pathway in Plants," *Annu. Rev. Plant Physiol. Plant Mol. Biol.* 46:521–547 (1995).

Chappell et al., "Is the Reaction Catalyzed by 3–Hydroxy–3–Methylglutaryl Coenzyme A Reductase a Rate–Limiting Step for Isoprenoid Biosynthesis in Plants," *Plant Physiol.* 109:1337–1343 (1995).

Chappell, "The Biochemistry and Molecular Biology of Isoprenoid Metabolism," *Plant Physiol.* 107:1–6 (1995).

Chen et al., "Cloning, Expression, and Characterization of (+)–δ–Cadinene Synthase: A Catalyst for Cotton Phytoalexin Biosynthesis," *Arch. Biochem. Biophys.* 324:255–266 (1995).

Chiu et al., "Engineered GFP as a vital reporter in plants," *Current Biology* 6:325–330 (1996).

Colby et al., "4S–Limonene Synthase from the Oil Glands of Spearmint (*Mentha spicata*)," *J. Biol. Chem.* 268:23016–23024 (1993).

Cortes et al., "Repositioning of a Domain in a Modular Polyketide Synthase to Promote Specific Chain Cleavage," *Science* 268:1487–1489 (1995).

Croteau et al., "Biosynthesis of Monoterpenes: Partial Purification, Characterization, and Mechanism of Action of 1,8–Cineole Synthase," *Arch. Biochem. Biophys.* 309:184–192 (1994).

Dixon et al., "Phytoalexin Induction in French Bean," *Plant Physiol.* 71:251–256 (1983).

El–Feraly et al., "EPI–Deoxyarteannuin B and 6,7–Dehydroartemisinic Acid from *Artemisia Annua*," *J. Nat. Prod.* 52:196–198 (1989).

Elakovich, "Sesquiterpenes as Phytoalexins and Allelopathic Agents," *Ecology and Metabolism of Plant Lipids* 325:93–108 (1986).

Enzell et al., "Mass spectra of tobacco isoprenoids," *Mass Spectrometry Rev.* 3:395 (1984).

Facchini et al., "Gene Family for an Elicitor–Induced Sesquiterpene Cyclase in Tobacco," *Proc. Natl. Acad. Sci. USA* 89:11088–11092 (1992).

Frohman et al., "Rapid production of full–length cDNAs from rare transcripts: Amplification using a single gene–specific oligonucleotide primer," *Proc. Natl. Acad. Sci. USA* 85:8998–9002 (1988).

Gambliel et al., "Pinene Cyclases I and II," *J. Biol. Chem.* 259:740–748 (1984).

Gibson et al., "Wild potato repels aphids by release of aphid alarm pheromone," *Nature* 302:608–609 (1983).

Guo et al., "Biosynthesis of the Diterpene cis–Abienol in Cell–Free Extracts of Tobacco Trichomes," *Arch. Biochem. Biophys.* 308:103–108 (1994).

Habtermariam et al., "A New Antibacterial Sesquiterpene From *Premna Oligotricha*," *J. Natl. Prod.* 56:140–143 (1993).

Hohn et al., "Isolation and nucleotide sequence of a sesquiterpene cyclase gene from the trichothecene–producing fungus *Fusarium sporotrichioides*," *Gene* 79:131–138 (1989).

Hohn et al., "Purification and Characterization of the Sesquiterpene Cyclase Aristolochene Synthase from *Penicillium roqueforti*," *Arch. Biochem. Biophys.* 272:137–143 (1989).

Hohn et al., "Purification and Characterization of the Sesquiterpene Cyclase Trichodiene Synthetase from *Fusarium sporotrichioides*," *Arch. Biochem. Biophys.* 251:756–761 (1986).

Joly et al., "Effect of Site–directed Mutagenesis of Conserved Asparate and Arginine Residues upon Farnesyl Diphosphate Synthase Activity," *J. of Biol. Chem.* 268:26983–26989 (1993).

(List continued on next page.)

*Primary Examiner*—Sheela Huff
*Attorney, Agent, or Firm*—Clark & Elbing, LLP

[57] ABSTRACT

Disclosed is a chimeric isoprenoid synthase polypeptide including a first domain from a first isoprenoid synthase joined to a second domain from a second, heterologous isoprenoid synthase, whereby the chimeric isoprenoid synthase is capable of catalyzing the production of isoprenoid reaction products that are not produced in the absence of the second domain of the second, heterologous isoprenoid synthase. Also disclosed is a chimeric isoprenoid synthase polypeptide including an asymmetrically positioned homologous domain, whereby the chimeric isoprenoid synthase is capable of catalyzing the production of isoprenoid reaction products that are not produced when the domain is positioned at its naturally-occurring site in the isoprenoid synthase polypeptide.

10 Claims, 9 Drawing Sheets-

OTHER PUBLICATIONS

Kalsi et al., "Stereostructures of Two Biologically Active Sesquiterpene Lactones from *Inula Racemosa*," *Phytochemistry* 28:2093–2096 (1989).

Koepp et al., "Cyclization of Geranylgeranyl Diphosphate to Taxa–4(5), 11(12)–diene Is the Committed Step of Taxol Biosynthesis in Pacific Yew," *J. Biol. Chem.* 270:8686–8690 (1995).

Kubo et al., "Potentiation of antifungal activity of sesquiterpene dialdehydes against *Candida albicans* and two other fungi," *Experientia* 48:1162–1164 (1992).

Kurosaki, "Dissociation of Dimeric 6–Hydroxymellein Synthase, a Polyketide Biosynthetic Enzyme in Carrot Cell Extracts, with Loss of Keto–Reducing Activity," *Archives of Biochem. and Biophys.* 321:239–244 (1995).

Lee et al., "Sesquiterpene Antitumor Agents: Inhibitors of Cellular Metabolism," *Science* 196:533–536 (1977).

Mabry et al., "Sesquiterpene Lactones and Other Terpenoids," *Herbivores, Their Interaction with Secondary Plant Metabolites,* 14:501–537 (1979).

McDaniel et al., "Rational design of aromatic polyketide natural products by recombinant assembly of enzymatic subunits," *Nature* 375:549–554 (1995).

Midland et al., "The Structure of Syringolides 1 and 2, Novel C–Glycosidic Elicitors from *Pseudomonas syringae* pv. tomato," *J. Org. Chem.* 58:2940–2945 (1993).

Moesta et al., "Casbene Synthetase: Regulation of Phytoalexin Biosynthesis in *Ricinus communis* L Seedlings," *Arch. Biochem. Biophys.* 238:325–333 (1985).

Munck et al., "Purification and Characterization of the Sesquiterpene Cyclase Patchoulol Synthase from *Pogostemon cablin*," *Arch. Biochem. Biophys.* 282:58–64 (1990).

Proctor et al., "Isolation, Characterization, and Bacterial Expression of a Sesquiterpenoid Biosynthetic Gene (Aril) from *Penicillium Roqueforti*," *J. Biol. Chem.* 268:4543–4548 (1993).

Russell et al., "A Sesquiterpenoid Ant Repellent from *Dysoxylum Spectabile*," *Phytochemistry* 35:1455–1456 (1994).

Ruzicka, "The Isoprene Rule and the Biogenesis of Terpenic Compounds," *Experientia* 10:357–396 (1953).

Savage et al., "Monoterpene Synthases of *Pinus contorta* and Related Conifers," *J. Biol. Chem.* 269:4012–4020 (1994).

Smith et al., "The Syringolides: Bacterial C–Glycosyl Lipids That Trigger Plant Disease Resistance," *Tetrahedron Letters* 34:223–226 (1993).

Stevens, "Biological Activity and Chemistry of Sesquiterpene Lactones," *Sesquiterpene Lactones* pp. 65–80 (1984).

Vögeli et al., "Purification and Characterization of an Inducible Sesquiterpene Cyclase from Elicitor–Treated Tobacco Cell Suspension Cultures," *Plant Physiol.* 93:182–187 (1990).

Alonso et al., "Purification of 4S–Limonene Synthase, a Monoterpene Cyclase from the Glandular Trichomes of peppermint (*Mentha x piperita*) and Spearmint (*Mentha spicata*)," *J. Biol. Chem.* 267:7582–7587 (1992).

Anke and Sterner, "Comparison of the Antimicrobial and Cytotoxic Activities of Twenty Unsaturated Sesquiterpene Dialdehydes from Plants and Mushrooms," *Planta Med.* 57:344–346 (1991).

Ave et al., "Aphid repellent sesquiterpenes in glandular trichomes of *Solanum berthaultii* and *S. tuberosum*," *Entomologia Experimentalis et Applicata* 44:131–138 (1987).

Back et al., "Expression of a Plant Sesquiterpene Cyclase Gene in *Escherichia coli*," *Arch. Biochem. Biophys.* 315:527–532 (1994).

Back et al. "Cloning and Bacterial Expression of a Sesquiterpene Cyclase from *Hyoscyamus muticus* and Its Molecular Comparison to Related Terpene Cyclases," *J. Biol. Chem.* 270:7375–7381 (1995).

Barnby et al. "Effects of Azadirachtin on Levels of Ecdysteroids and Prothoracicotropic Hormone–Like Activity in *Heliothis Virescens* (Fabr.) Larvae," *J. Insect. Physiol.* 36:125–131 (1990).

Borman, "Scientists Mobilize to Increase Supply of Anticancer Drug Taxol," *Chemical & Engineering News* 11–18 (1991).

Bowers et al., "Sesquiterpene Progenitor, Germacrene A: An Alarm Pheromone in Aphids," *Science* 196:680–681 (1977).

FARNESYL DIPHOSPHATE (+)-GERMACRENE A

EUDESMANE CARBOCATION 5-epi-ARISTOLOCHENE (*Nicotiana Tabacum*)

VETISPIRADIENE (*Hyoscyamus Muticus*)

| | | Hinc II | | | DOMINANT REACTION PRODUCTS [a] | | SPECIFIC ACTIVITY |
| --- | --- | --- | --- | --- | --- | --- | --- |
| | | Xba 1 | | Xba 1 | TEAS SPECIFIC | HVS SPECIFIC | nmol/mg prot • h |
| NH$_3$+ | HindIII | Nde 1 342 | Cla 1 | 532 | | | |
| TEAS | 152 | 281 | 379 442 | COO⁻ 548 aa | 100% | - | 47 |
| | HindIII | Nde 1 | | | | | |
| HVS | 160 | 268 | | COO⁻ 566 aa | - | 100 | 28 |
| | HindIII | | | | | | |
| CH 1 | TEAS | HVS | | | - | 100 | 35 |
| | | Nde 1 | | | | | |
| CH 2 | | | | | - | 100 | 22 |
| | | | Cla 1 | | | | |
| CH 3 | | | | | 100 | - | 21 |
| | | | Hinc II | | | | |
| CH 4 | | | | | 66 | 34 | 40 |
| | HindIII | | | | | | |
| CH 5 | | | | | 100 | - | 3 |
| | HindIII | | Cla 1 | | | | |
| CH 6 | | | | | 100 | 0 | 27 |
| | | Nde 1 | | | | | |
| CH 7 | | | | | NO ENZYME ACTIVITY | | - |
| | | Nde 1 | Cla 1 | | | | |
| CH 8 | | | | | NO ENZYME ACTIVITY | | - |
| | HindIII | Nde 1 | | | | | |
| CH 9 | | | | | - | 100 | 63 |
| | Hind III | | Hinc II | | | | |
| CH 10 | | | | | 68 | 34 | 25 |
| | | Nde 1 | Hinc II | | | | |
| CH 11 | | | | | 61 | 39 | 28 |
| | | | Hinc II | | | | |
| CH 12 | | | | | 73 | 27 | 27 |
| | | | Cla 1 | | | | |
| | | Xba 1 | | | | | |
| CH 13 | | | | | 23 | 77 | 60 |
| | | Nde 1 Xba 1 | | | | | |
| CH 14 | | | | | 33 | 67 | 37 |

CHIMERIC ISOPRENOID SYNTHASES AND USES THEREOF

CROSS REFERENCE TO RELATED APPLICATION

This application is a continuation of U.S. Ser. No. 08/631,341, filed Apr. 12, 1996, now U.S. Pat. No. 5,824,774, hereby incorporated by reference.

STATEMENT AS TO FEDERALLY SPONSORED RESEARCH

This invention was made in part with Government funding, and the Government therefore has certain rights in the invention.

BACKGROUND OF THE INVENTION

This invention relates to modified isoprenoid synthase enzymes, their encoding genes, and uses thereof.

The term isoprenoid is used to refer to a family of compounds derived from the isoprene building block. In particular, plant isoprenoids comprise a structurally diverse group of compounds that can be divided into classes of primary and secondary metabolites (FIG. 1). Isoprenoids that are primary metabolites include sterols, carotenoids, growth regulators, and the polyprenol substituents of dolichols, quinones, and proteins. These compounds are essential for membrane integrity, photoprotection, orchestration of developmental programs, and anchoring essential biochemical functions to specific membrane systems, respectively. Isoprenoids that are classified as secondary metabolites include monoterpenes, sesquiterpenes, and diterpenes. These compounds are said to mediate important interactions between plants and their environment. For example, specific terpenoids have been correlated with plant-plant (Stevens, In: *Isopentoids in Plants,* Nes, W. D. Fuller, G., and Tsai, L.-S., eds., Marcel Dekker, New York, pp. 65–80, 1984), plant-insect (Gibson and Pickett, *Nature* 302:608, 1983), and plant-pathogen interactions (Stoessl et al., *Phytochemistry* 15:855, 1976).

The common denominator for this diverse array of compounds is their universal five-carbon building block, isoprene. The "biogenic isoprene rule" was employed to rationalize the biosynthetic origins of all terpenoids derived from isoprene (Ruzicka, *Experientia* 10:357, 1953). The polymerization of two diphosphorylated isoprene building blocks (e.g., IPP and dimethylallyl) generates geranyl diphosphate (GPP), a linear C10 intermediate that can be converted to cyclic or linear end-products representing the monoterpenes, or used in another round of polymerization. The addition of a third isoprene unit to GPP generates farnesyl diphosphate (FPP), which can also be converted to cyclic or linear products representing the sesquiterpene class. Continuing the polymerization and chemical differentiation cycle leads to the production of other classes of terpenoids named according to the number of isoprene building blocks leading to their biosynthesis, for example, the addition of a third IPP to FPP generates geranylgeranyl diphosphate (GGPP).

These polymerization reactions are catalyzed by prenyltransferases that direct the attack of a carbocation (an electron deficient carbon atom resulting from the loss of the diphosphate moiety of one substrate) to an electron-rich carbon atom of the double bond on the IPP molecule (FIG. 2). The electrophilic nature of these reactions is said to be unusual relative to more general nucleophilic condensation reactions, but this appears to be a common reaction among isoprenoid biosynthetic enzymes and especially those enzymes involved in catalyzing the cyclization of various isoprenoid intermediates (Gershenzon and Croteau, In: *Lipid Metabolism in Plants,* Moore, T. S., ed., CRC Press, Boca Raton, Fla., pp. 340–388). The enzymes responsible for the cyclization of GPP, FPP, and GGPP are referred to as monoterpene, sesquiterpene, and diterpene synthases or synthases, and represent reactions committing carbon from the general isoprenoid pathway to end products in the monoterpene, sesquiterpene, and diterpene classes, respectively.

Two important biochemical distinctions between the prenyltransferase and synthase reactions are illustrated in FIG. 2. The prenyltransferases catalyze carbon-carbon bond formation between two substrate molecules, whereas the synthases catalyze an intramolecular carbon-carbon bond formation. The prenyltransferases also catalyze reactions with very little variance in the stereochemistry or length of the ensuing polymer. Prenyltransferases differ in the length of the allyic substrates that can be accepted in initiating these reactions. The synthases are also substrate specific. However, diverse sesquiterpene synthases, for example, can utilize the same substrate to produce different reaction products.

The biosynthesis of isoprenoids such as cyclic terpenes is said to be determined by key branch point enzymes referred to as terpene synthases. The reactions catalyzed by terpene synthases are complex, intramolecular cyclizations that may involve several partial reactions. For example, the bioorganic rationale for the cyclization of FPP by two sesquiterpene synthases are shown in FIG. 3. In step 1, the initial ionization of FPP is followed by an intramolecular electrophillic attack between the carbon bearing the diphosphate moiety and the distal double bond to form germacene A, a macrocylic intermediate. Internal ring closure and formation of the eudesmane carbonium ion constitutes step 2. For tobacco 5-epi-aristolochene synthase (TEAS), the terminal step is a hydride shift, methyl migration, and deprotonation at C9 giving rise to 5-epi-aristolochene as depicted in step 3*a*. *Hyoscyamus muticus* vetispiradiene synthase (HVS) shares a common mechanism at steps 1 and 2, but differs from TEAS in the third partial reaction in which a ring contraction would occur due to alternative migration of an electron pair. In each case, a monomeric protein of approximately 64 kD catalyzes the complete set of partial reactions and requires no cofactors other than $Mg^{+2}$.

SUMMARY OF THE INVENTION

In general, the invention features a chimeric isoprenoid synthase polypeptide including a first domain from a first isoprenoid synthase joined to a second domain from a second, heterologous isoprenoid synthase, whereby the chimeric isoprenoid synthase is capable of catalyzing the production of isoprenoid reaction products that are not produced in the absence of the second domain of the second, heterologous isoprenoid synthase. In preferred embodiments, the chimeric isoprenoid synthase is capable of catalyzing at least two different isoprenoid reaction products; the isoprenoid reaction products are cyclic; the second domain of the second, heterologous isoprenoid synthase also determines the ratio of the isoprenoid reaction products of the chimeric isoprenoid synthase; the first domain from the first isoprenoid synthase is a plant isoprenoid synthase and the second domain from the second, heterologous isoprenoid synthase is also from a plant isoprenoid synthase.

Preferably, the chimeric isoprenoid synthase is chosen from the group consisting of (a) the tobacco-Hyoscyamus CH4 chimeric isoprenoid synthase; (b) the tobacco-Hyoscyamus CH10 chimeric isoprenoid synthase; (c) the tobacco-Hyoscyamus CH11 chimeric isoprenoid synthase; (d) the tobacco-Hyoscyamus CH12 chimeric isoprenoid synthase; (e) the tobacco-Hyoscyamus CH13 chimeric isoprenoid synthase; or (f) the tobacco-Hyoscyamus CH14 chimeric isoprenoid synthase, all as described herein.

In preferred embodiments, the chimeric isoprenoid synthase catalyzes the production of an isoprenoid reaction product that is of agricultural, pharmaceutical, commercial, or industrial significance (e.g., an antifungal agent, antibacterial agent, or antitumor agent).

In other related aspects, the invention features DNA, vectors, and cells (for example, *E. coli, Saccharomyces cerevisiae,* animal or plant cells) encoding or containing a chimeric isoprenoid synthase polypeptide.

In another aspect, the invention features a chimeric isoprenoid synthase polypeptide including an asymmetrically positioned homologous domain whereby the chimeric isoprenoid synthase is capable of catalyzing the production of isoprenoid reaction products (preferably, cyclic products) when the domain is positioned at its naturally-occurring site in the isoprenoid synthase polypeptide.

In another aspect, the invention features a method for producing a chimeric isoprenoid synthase polypeptide, the method involving: (a) providing a cell transformed with DNA encoding a chimeric isoprenoid synthase positioned for expression in the cell; (b) culturing the transformed cell under conditions for expressing the DNA; and (c) recovering the chimeric isoprenoid synthase.

By "isoprenoid synthase" is meant a polypeptide that is capable of catalyzing a reaction involving the intramolecular carbon-carbon bond formation of an allylic diphosphate substrate (for example, a $C_{10}$, $C_{15}$, or $C_{20}$ allylic diphosphate substrate) to an isoprenoid product (for example, a monoterpene, diterpene, sesquiterpene, or sterol product). Examples of such isoprenoid synthases include, without limitation, monoterpene synthases (for example, limonene synthase), diterpene synthases (for example, casbene synthase), and sesquiterpene synthases (for example, 5-epi-aristolochene synthase, vetispiradiene synthase, and cadinene synthase) that are responsible for cyclization of geranyl diphosphate (GPP), farnesyl diphosphate (FPP), and geranylgeranyl diphosphate (GGPP), respectively. A number of terpene synthases from plant and microbial sources have been isolated and characterized (see, for example, Moestra and West, *Arch. Biochem. Biophys.* 238:325, 1985; Hohn and Van Middlesworth, *Arch. Biochem. Biophys.* 251:756, 1986; Hohn and Plattner, *Arch. Biochem. Biophys.* 272:137, 1989; Cane and Pargellis, *Arch. Biochem. Biophys.* 254:421, 1987; Munck and Croteau, *Arch. Biochem. Biophys.* 282:58, 1990; Alonso et al., *J. Biol. Chem.* 267:7582, 1992; Savage et al., *J. Biol. Chem.* 269:4012, 1994; Croteau et al., *Arch. Biochem. Biophys.* 309:184, 1994; Vögeli et al., *Plant Physiol.* 93:182, 1990; Guo et al., *Arch. Biochem. Biophys.* 308:103, 1994; and Gambliel and Croteau, *J. Biol. Chem.* 259:740, 1984). In general, terpene synthases are soluble enzymes having a molecular weight of about 40 to 100 kD. Genes encoding a number of monoterpene, diterpene, and sesquiterpene synthases have been described for a number of plant and microbial organisms (see, for example, Hohn and Beremand, *Gene* 79:131, 1989; Proctor and Hohn, *J. Biol. Chem.* 268:4543, 1993; Facchini and Chappell, *Proc. Natl. Acad. Sci.* 89:11088, 1992; Back and Chappell, *J. Biol. Chem.* 270:7375, 1995; Colby et al., *J. Biol. Chem.* 268:23016, 1993; Mau and West, *Proc. Natl. Acad. Sci.* 91:8497, 1994; Chen et al., *Arch. Biochem. Biophys.* 324:255, 1994; and Cane et al., *Biochemistry* 33:5846, 1994).

By "polypeptide" or "protein" is meant any chain of amino acids, regardless of length or post-translational modification (for example, glycosylation or phosphorylation).

By "joined to" is meant covalently bonded either directly or indirectly (i.e., the domains are separated by an intervening amino acid sequence). Such domains may be bonded by any means, including, without limitation, a peptide bond or chemical linkage.

By "domain" is meant a contiguous stretch of amino acids within a polypeptide or protein.

By "isoprenoid" is meant a compound that is derived from an isoprene building block. In particular, isoprenoid compounds include, without limitation, monoterpenes, diterpenes, sesquiterpenes, and sterols. As described herein, isoprenoids are found in a variety of organisms, for example, animal, fungal, or bacterial sources.

By "asymmetrically positioned" is meant located within the chimeric polypeptide at a site which differs from its position in the naturally-occurring polypeptide.

By "heterologous" is meant derived from different sources (in this case, different polypeptides).

By "homologous" is meant derived from the same source (in this case, the same polypeptide).

Other features and advantages of the invention will be apparent from the following description of the preferred embodiments thereof, and from the claims.

DETAILED DESCRIPTION

The drawings will first be described.

Drawings

Figure 1:
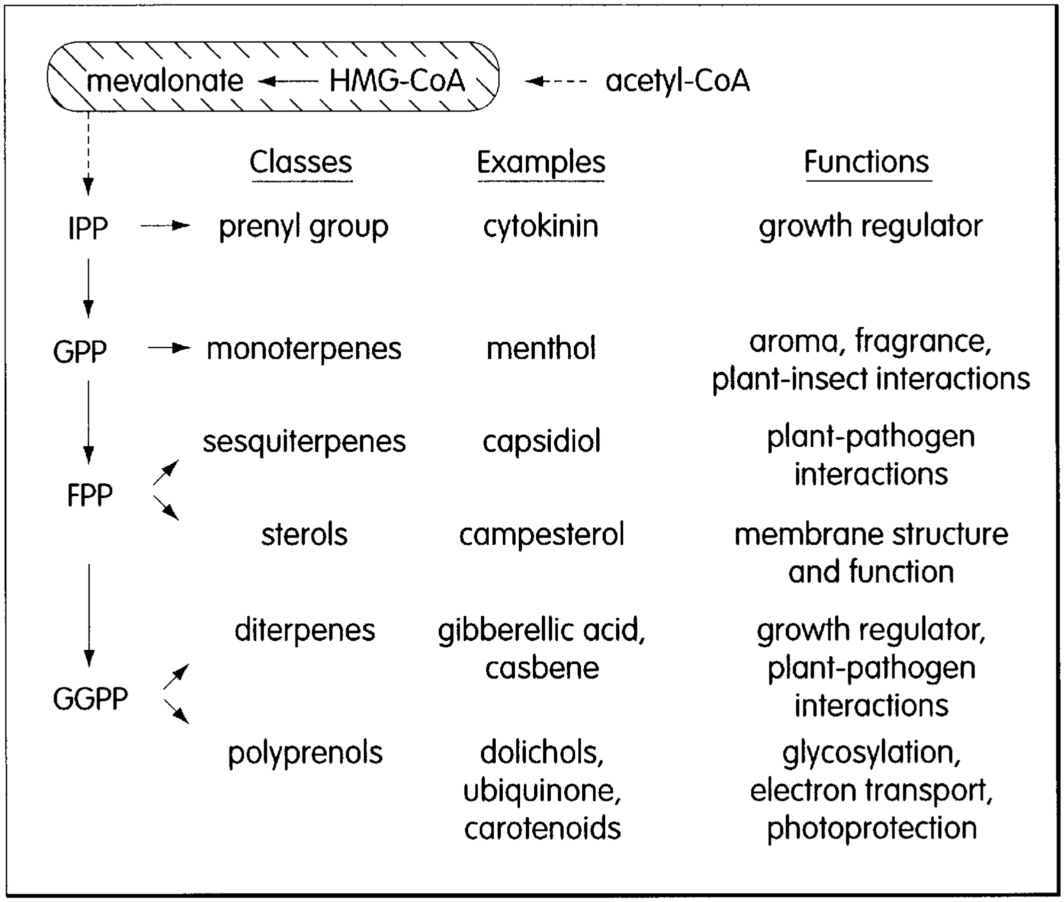
FIG. 1 is a schematic illustration showing the isoprenoid biosynthetic pathway with respect to the type of end products and their respective physiological functions. Broken arrows indicate multiple steps or reactions.
Figure 2:
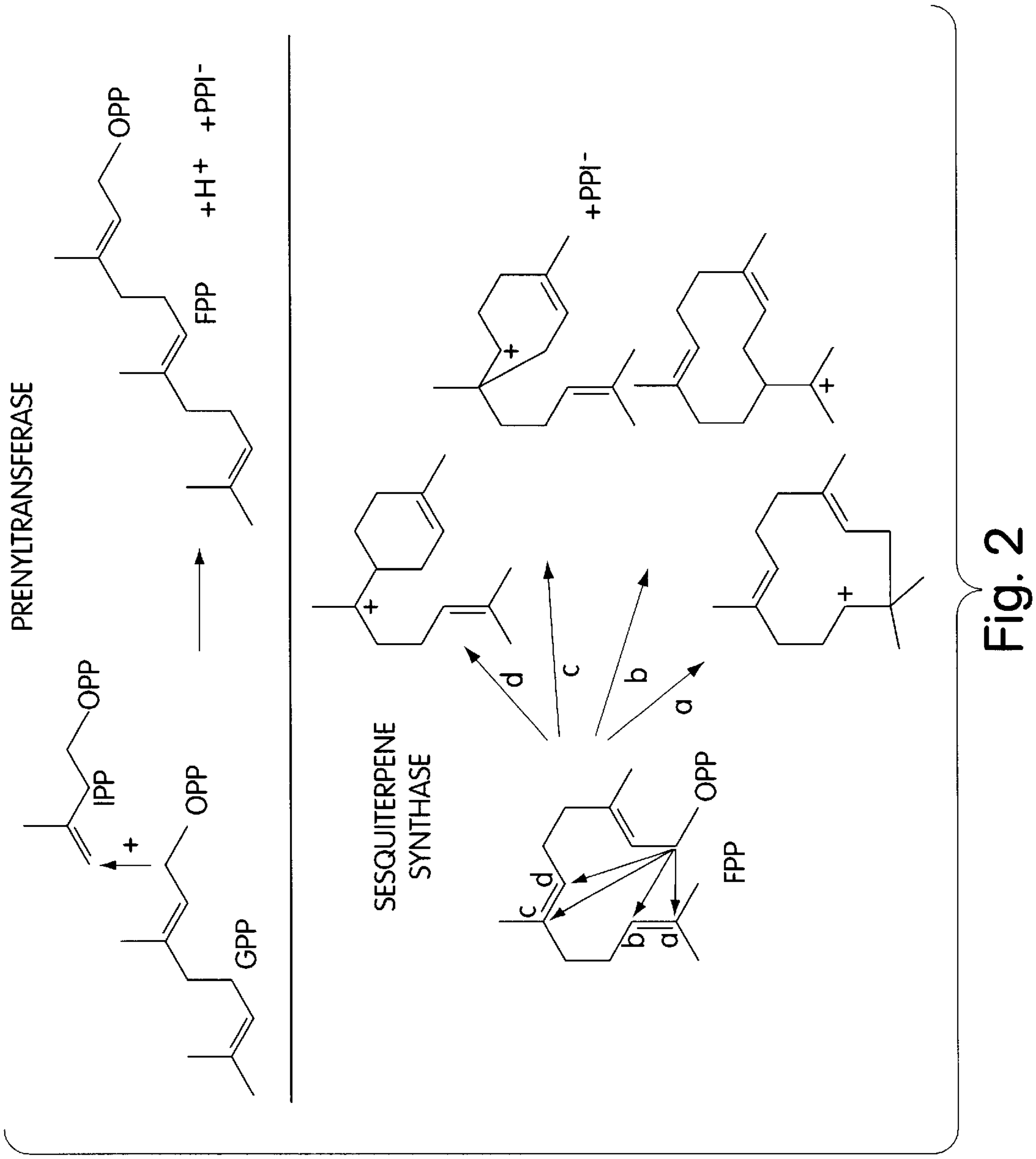
FIG. 2 is a schematic illustration showing the various reactions that are catalyzed by prenyltransferases and terpene synthases.
Figure 3:
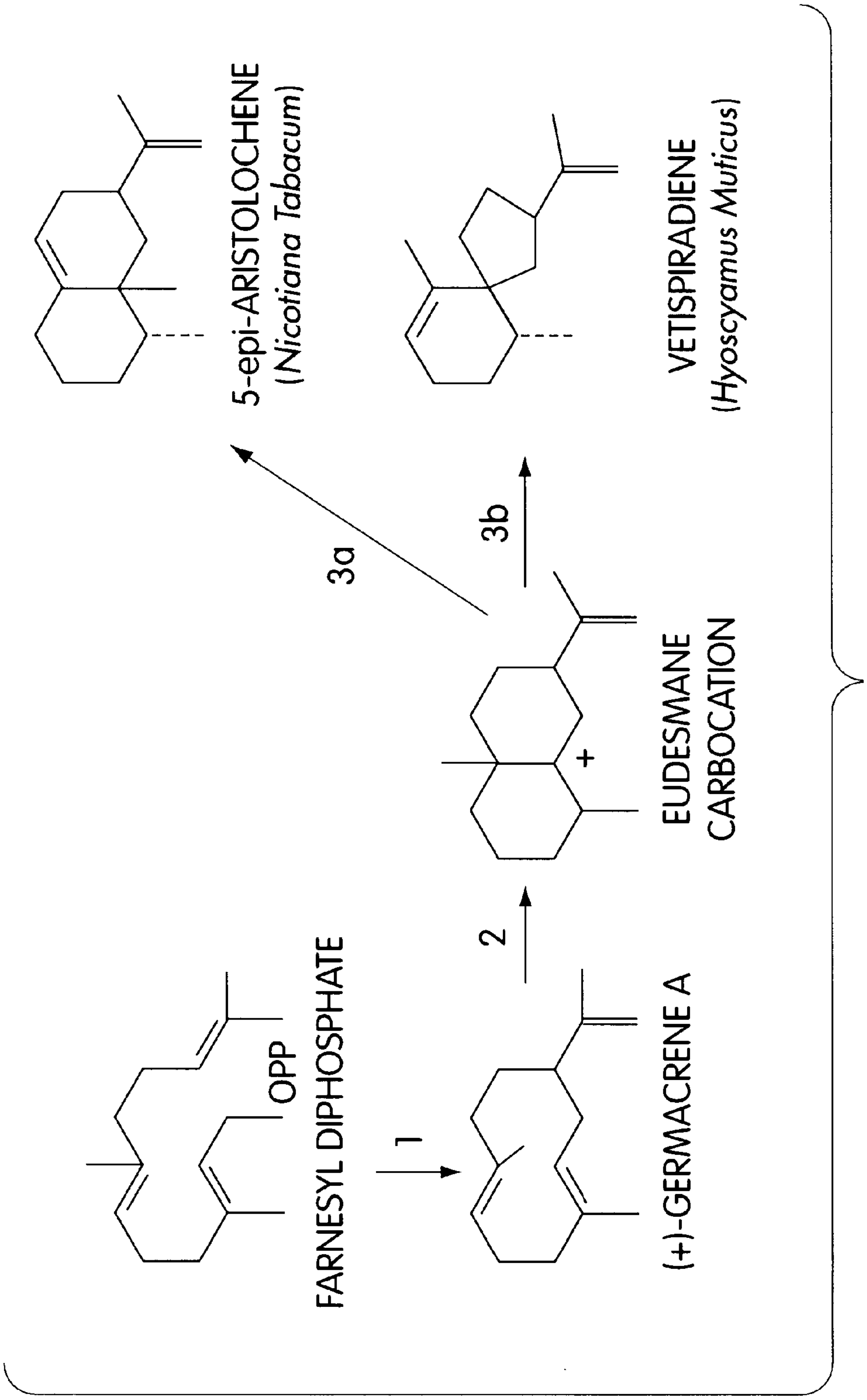

FIG. 3 is a schematic illustration showing a reaction mechanism for the synthesis of eremophilane (tobacco 5-epi-aristolochene synthase, TEAS) and vetispiradiene (Hyoscyamus vetispiradiene synthase, HVS) type sesquiterpene synthases. Partial reactions 1 and 2 are considered common to both types of synthases. Mechanistic differences in partial reactions 3*a* and 3*b* are sufficient to account for the different reaction products shown.

Figure 4A:
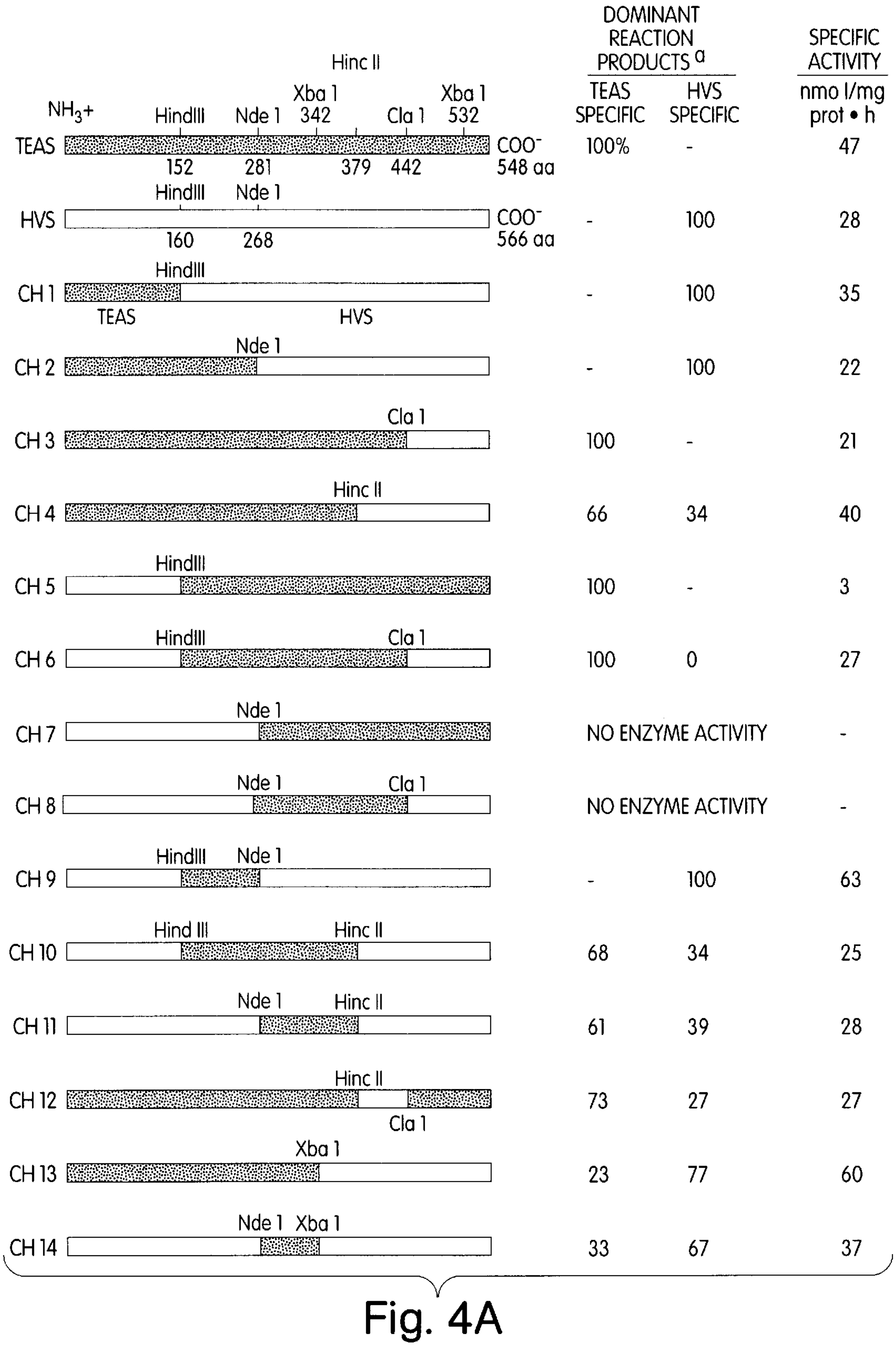

FIG. 4A is a schematic illustration showing the chimeric constructs used to map catalytic domains within sesquiterpene synthases. Line drawings depict composite diagrams for wildtype (i.e., TEAS and HVS) and chimeric (CH1–CH14) sesquiterpene synthase genes that were engineered into the bacterial expression vector pGBT-T19. Gene constructs were prepared using a combination of the available restriction endonuclease sites and amplification of select regions using PCR and PCR primers harboring convenient restriction endonuclease sites. Correspondence between unique restriction endonuclease sites and amino acid positions are noted.

Figure 4B:
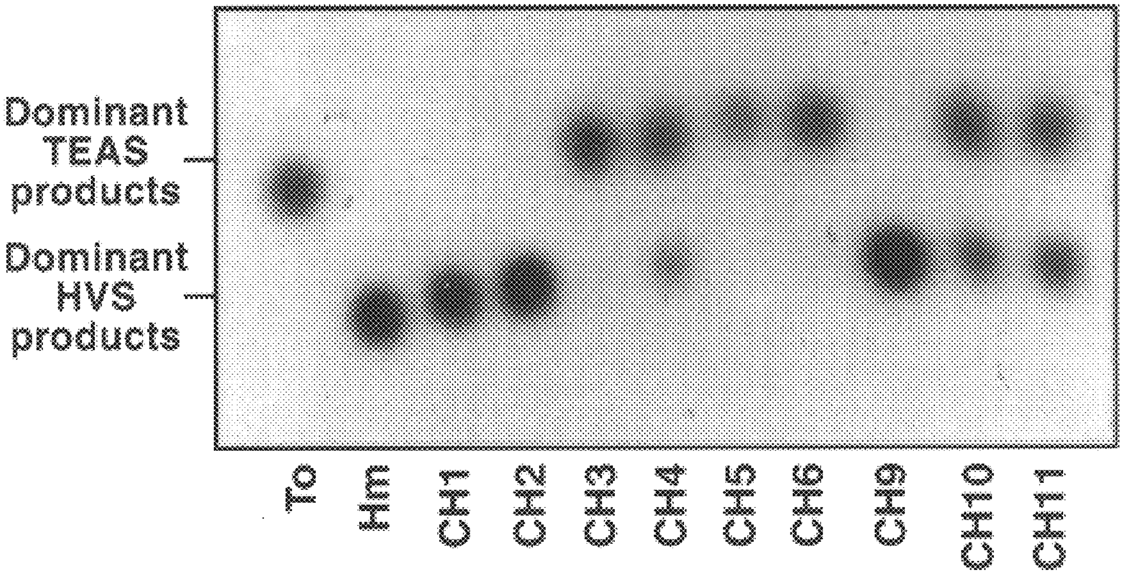

FIG. 4B is a photograph of a TLC experiment showing synthase enzyme activities in sonicated lysates of *E. coli* TB 1 cells expressing the TEAS, HVS, and chimeric synthase constructs (CH1–CH14) and measured using $^{3}$H-FPP. Reaction products were separated by argentation-TLC and detected by autoradiography. The radioactivity in 0.5 mm segments of each lane of an argentation-TLC plate was determined in a scintillation counter, and radioactivity associated with the zones for the TEAS and HVS specific products was set to 100%.

Figure 5:
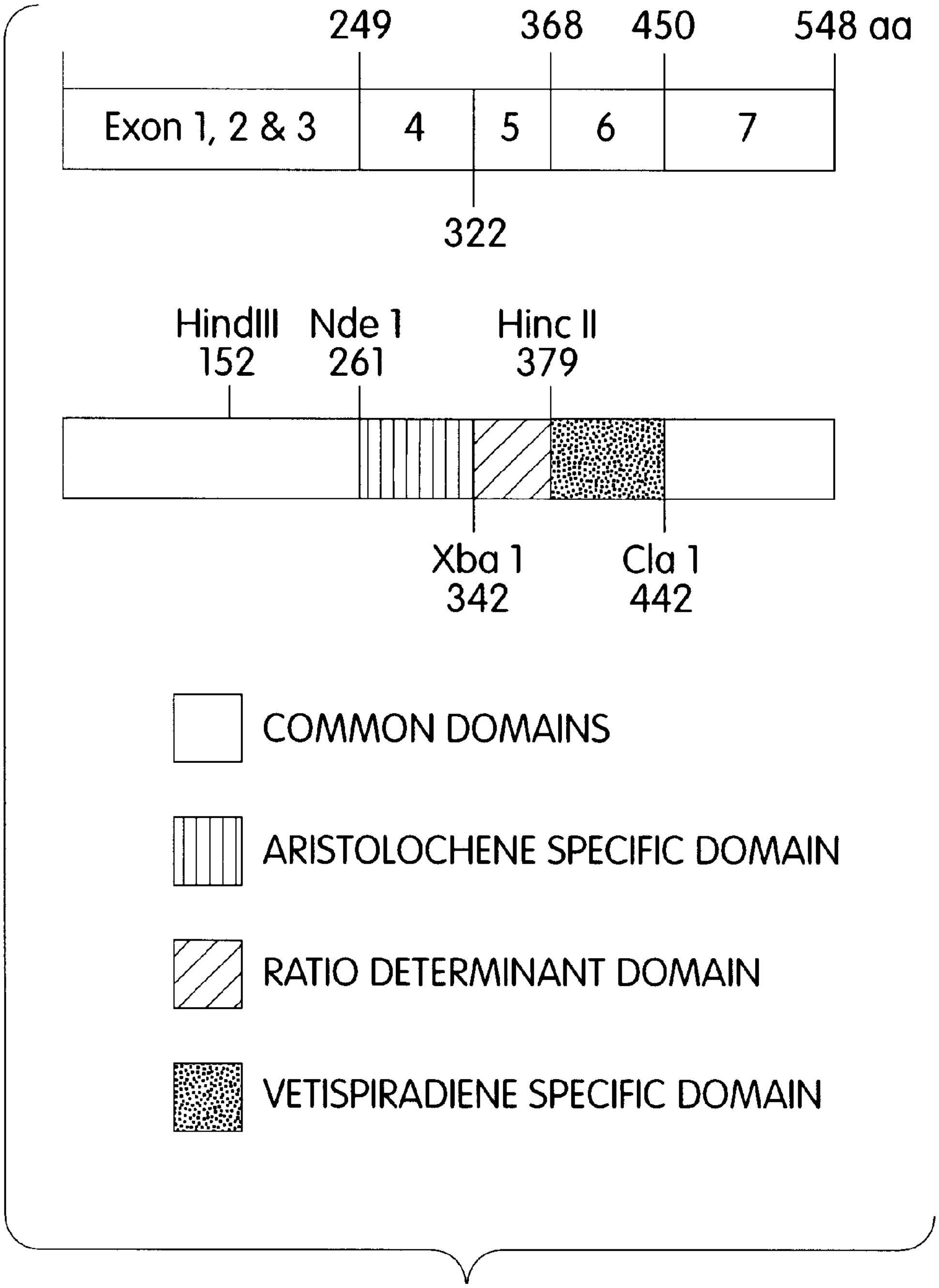

FIG. 5 is a schematic illustration showing the correspondence between exons and functional domains within isoprenoid synthases. The upper diagram represents the organization of exons within the TEAS gene, which is nearly identical to that of the HVS and casbene synthase genes. The lower diagram shows the alignment of functional domains to the exonic organization of the TEAS and HVS genes. Exon numbers are shown within the upper diagram, and all other numbers refer to amino acid positions, some of which correspond to the noted restriction endonuclease sites.

Figure 6:
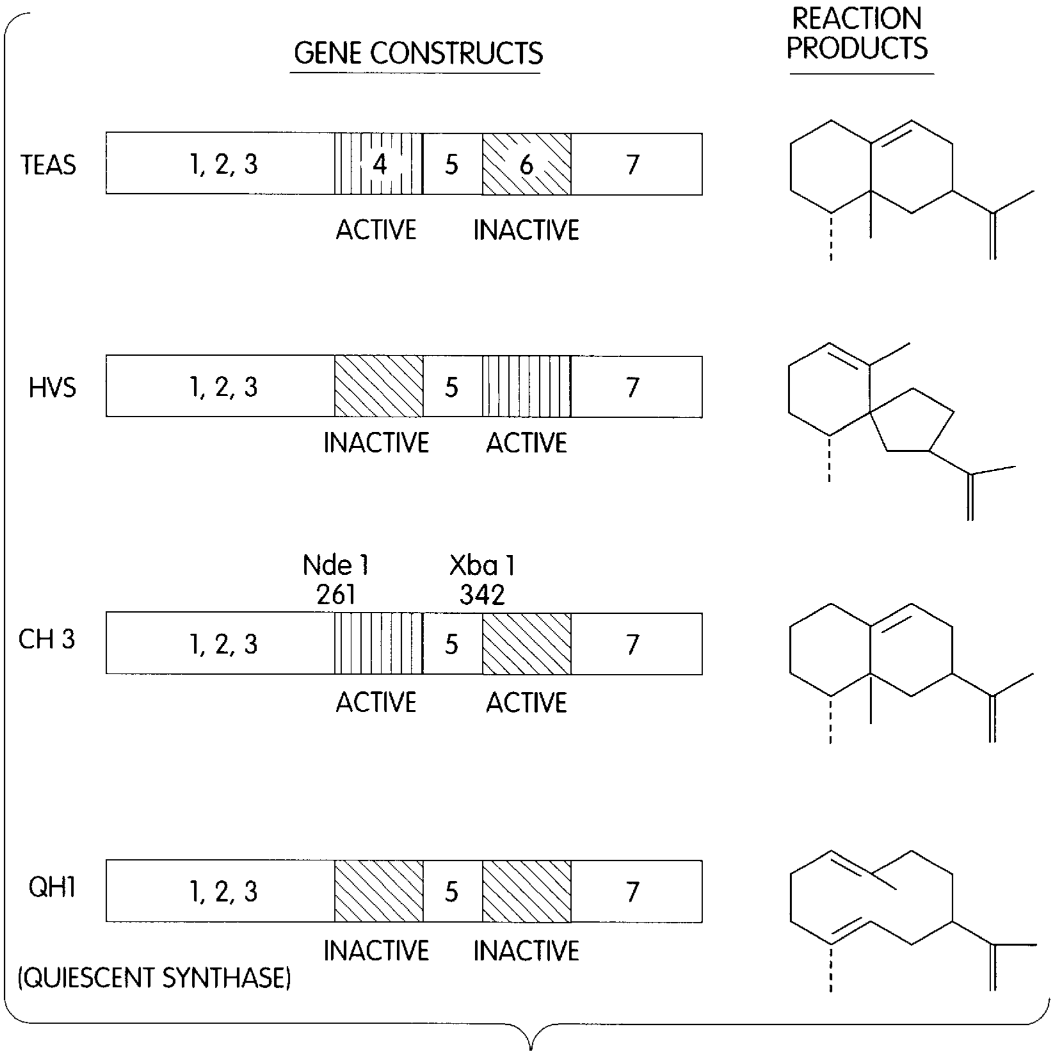

FIG. 6 is a schematic diagram showing a domain switching strategy used to generate a quiescent synthase (QH1). Substituting the inactive HVS domain corresponding to exon 4 into CH3 results in a synthase having an altered enzyme activity.

Figure 7:
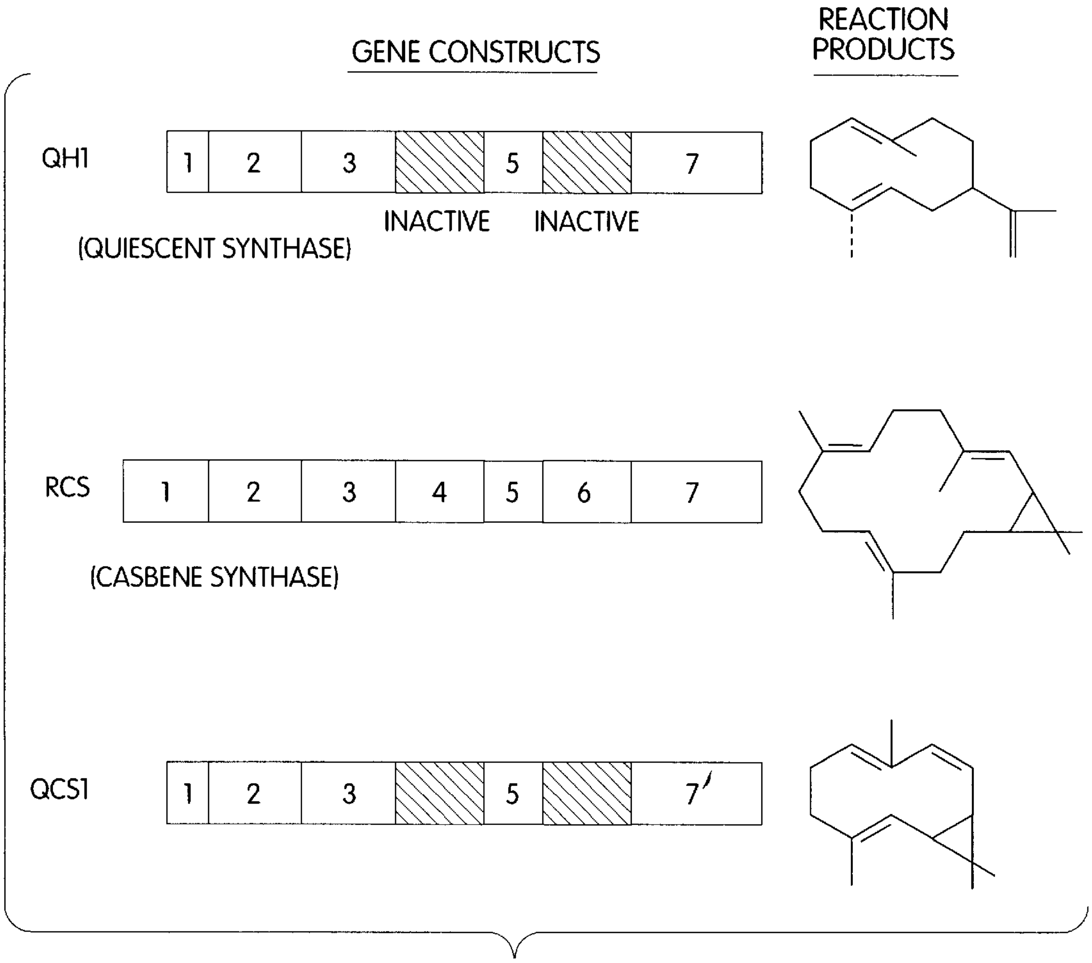

FIG. 7 is a schematic diagram of a domain switching strategy used for producing a chimeric quiescent-casbene synthase, and possible reaction products.

Figure 8:
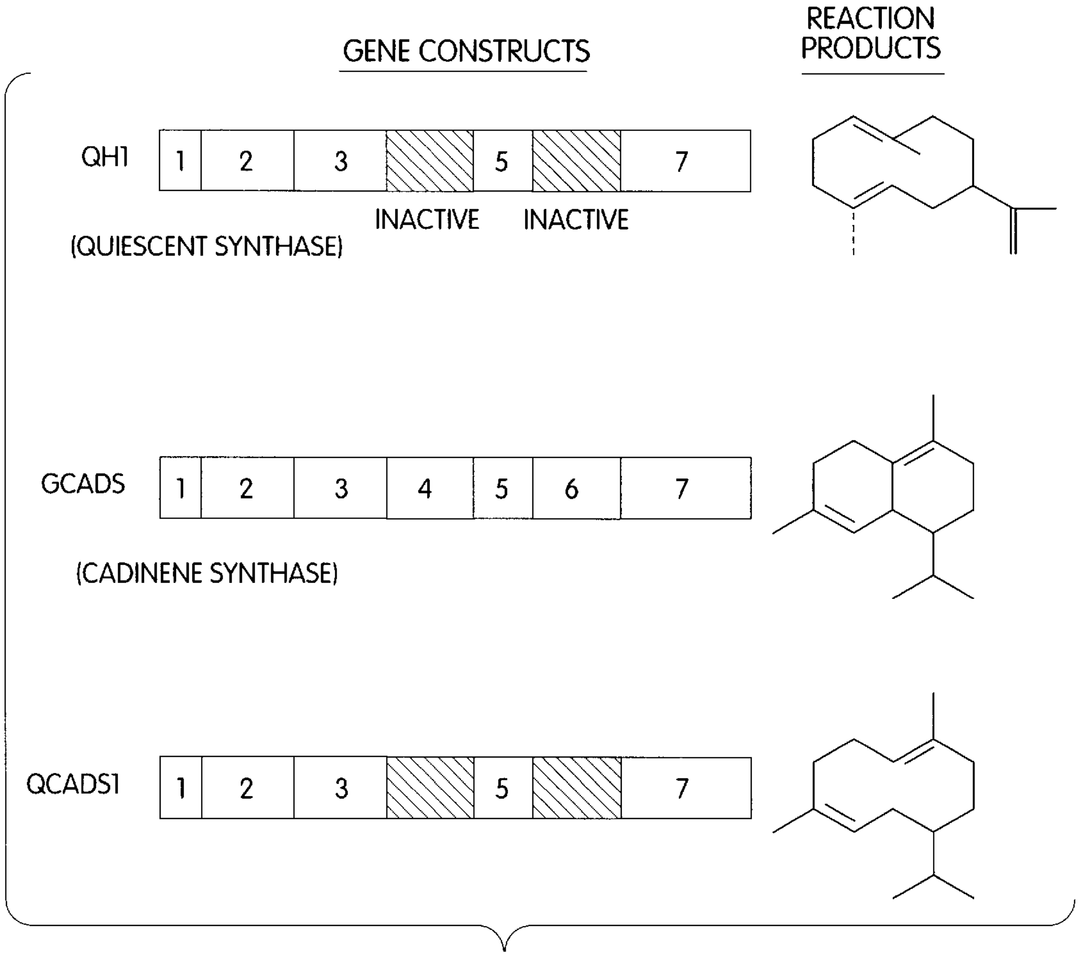

FIG. 8 is a schematic illustration of a domain switching strategy for producing a chimeric quiescent-cadinene synthase, and possible reaction products.

Chimeric Isoprenoid Synthases

Plasmids designed for expressing a chimeric synthase were generated by substituting a portion of a gene encoding a domain from tobacco 5-epi-aristolochene synthase with a portion of a gene encoding a domain from Hyoscyamus vetispiradiene synthase. These plasmids were expressed in bacteria, and bacterial lysates were prepared and assayed for sesquiterpene synthase activity. The sesquiterpene synthase assays included an argentation-thin layer chromatography (TLC) analysis which distinguished the aristocholene and vetispiradiene reaction products (Back and Chappell, *J. Biol. Chem.* 270:7375, 1995). As shown in FIG. 4A, fourteen chimeric synthase constructs were generated and were assayed as follows.

Full-length cDNAs for the tobacco 5-epi-aristolochene synthase (TEAS) and Hyoscyamus vetispiradiene synthase (HVS) were cloned into the EcoRI/XhoI sites of pBluescript SK (Stratagene), creating the pBSK-TEAS and pBSK-HVS plasmids, respectively (Back and Chappell, *J. Biol. Chem.* 270:7375, 1995). The TEAS and HVS cDNA inserts of these expression plasmids were oriented with their translation start codons neighboring the EcoRI restriction site and their 3' poly A tail flanked by the XhoI restriction site of the pSK plasmid.

Chimeric synthases CH1, CH2, CH5, and CH7 were constructed by utilizing the conserved HindIII and NdeI restriction sites found between the tobacco and Hyoscyamus genes. CH1 was prepared by ligating the 5' terminal portion of the TEAS gene (corresponding to the EcoRI to HindIII fragment) with the 3' terminal portion of HVS gene (corresponding to the HindIII to KpnI fragment) into the bacterial expression vector pGBT-T19 (Gold Biotechnology) predigested with EcoRI and KpnI.

CH2 was prepared by ligating the 5' terminal portion of the TEAS gene (corresponding to the EcoRI to NdeI fragment) with the 3' terminal portion of HVS gene (corresponding to the NdeI to KpnI fragment) into pGBT-T19.

CH5 was prepared by ligating the 5' terminal portion of the HVS gene (corresponding to the EcoRI to HindIII fragment) with the 3' terminal portion of TEAS gene (corresponding to the HindIII to KpnI fragment) into pGBT-T19.

CH7 was prepared by ligating the 5' terminal portion of the HVS gene (corresponding to the EcoRI to NdeI fragment) with the 3' terminal portion of TEAS gene (corresponding to the NdeI to KpnI fragment) into pGBT-T19.

CH3, CH4, CH12, and CH13 were constructed using conventional polymerase chain reaction (PCR) methodologies, with primers designed for the amplification of particular segments of the HVS gene. To facilitate directional cloning and maintenance of reading frame, primers were also designed to contain convenient restriction sites.

CH3 was constructed as follows. An EcoRI/ClaI restriction fragment of the TEAS gene was isolated and ligated to the ClaI/KpnI fragment of the HVS gene. The HVS ClaI/KpnI fragment was prepared by PCR methodology using 5'-d(GGG<u>ATCGAT</u>GACATAGCCACGTATGAGGTT)-3' (SEQ ID NO:1) (ClaI restriction site underlined) as the forward primer and 5'-d(AATACGACTCACTATAG)-3' (SEQ ID NO:2) as the reverse primer (corresponding to the T7 sequence found in the multiple cloning site of pBSK) using pBSK-HVS as the DNA template. The resulting restriction fragment was ligated into the EcoRI/KpnI sites of the pGBT-T19 vector.

CH4 and CH13 were constructed in a similar manner, but using the forward amplification primers 5'-d(CGA <u>GTCAAC</u>ATGGTTTATTGAGGGATA)-3' (SEQ ID NO:3) (HincII restriction site underlined) and 5'-d(TAT <u>TCTAGA</u>TCTCTATGACGATTATGAA)-3' (SEQ ID NO:4) (XbaI restriction site underlined), respectively.

CH12 was prepared by ligating a PCR fragment corresponding to the first 1326 nucleotides of CH4 with the ClaI/KpnI fragment of the TEAS gene into the EcoRI/KpnI sites of the pGBT-T19 vector. The CH4 fragment was prepared using forward amplification primer 5'-d (GGGAGCTC <u>GAATTC</u>CATGGCCTCAGCAGCAGTTGCAAACTAT)-3' (SEQ ID NO:5) (EcoRI restriction site underlined and translation start codon in bold) and reverse primer 5'-d(GGG <u>ATCGAT</u>AACTCTGCATAATGTAGCATT)-3' (SEQ ID NO:6) (ClaI restriction site underlined).

Chimeric synthases CH6, CH8, CH9, CH10, CH11, and CH14 were constructed as follows. Ligation of the EcoRI/HindIII fragment of the HVS gene with the HindIII/KpnI fragment of CH3 generated CH6. CH8 was created by ligating the EcoRI/NdeI fragment of HVS with the NdeI/KpnI fragment of CH3. CH9 was created by ligating the EcoRI/NdeI fragment of CH5 with the NdeI/KpnI fragment of HVS. CH10 was constructed by ligating the EcoRI/HindIII fragment of HVS with the HindIII/KpnI fragment of CH4. CH11 was constructed by ligating the EcoRI/NdeI fragment of HVS with the NdeI/KpnI fragment of CH4. And CH14 was generated by substituting the EcoRI/NdeI fragment of CH13 with the corresponding DNA fragment of pBSK-HVS. The nucleotide junctions of the chimeric constructs were confirmed by double-stranded DNA sequencing using the dideoxy nucleotide chain termination kit, according to the manufacturer's instructions (U.S. Biochemical Corp).

Chimeric synthases were expressed in *E. coli* TB1 cells. Procedures for growth of the bacterial cells, induction of gene expression, measurement of sesquiterpene synthase enzyme activity, and the determination of total protein in the bacterial lysates were performed according to the methods described by Back and Chappell (*Arch. Biochem. Biophys.* 315:527, 1994; *J. Biol. Chem.* 270:7375, 1995). Reaction products were separated by developing G60 silica TLC plates impregnated with 15% silver nitrate in benzene:hexane:diethyl ether (50:50:1). For qualitative evaluations, TLC plates were sprayed with Enhance surface fluorography spray (Dupont) and exposed to Kodak XAR-5 film for 2 to 5 days at −70° C. For quantitative evaluations, 0.5 mm zones of an entire lane from a TLC plates were scraped into scintillation vials, and the radioactivity was determined using a Packard 1500 Liquid Scintillation Counter. The dominant reaction products generated by the synthase activities resulting from expression of the TEAS, HVS, CH4, and CH14 constructs in bacterial lysates were also verified by gas chromatography (GC) and gas chromatography-mass spectroscopy (GC-MS) according to the conditions described by Chappell et al. (*Phytochemistry* 26:2259, 1987) (data not shown). In addition, mass spectra profiles were compared to that published for 5-epi-aristolochene (Anke and Sterner, *Planta Med.* 57:344, 1991) and the predicted fragmentation pattern for vetispiradiene (Enzell et al., *Mass Spectrometry Rev.* 3:395, 1984).

As shown in FIGS. 4A–B, the dominant reaction product resulting from the expression of the tobacco TEAS gene expressed was 5-epi-aristolochene, and vetispiradiene was found to be the dominant reaction product resulting from the expression of the HVS gene. The predominant reaction products generated by the expression of CH1 and CH2 were also HVS-specific (i.e., vetispiradiene), with enzyme specific activities similar to those found for HVS that was expressed from the pBSK-HVS plasmid. These results indicated that the amino-terminal half of TEAS and HVS were functionally equivalent with respect to the HVS carboxy-terminus and do not contribute to the specificity of the reaction product. CH7, having an HVS amino terminus and a TEAS carboxy terminus, is the converse construct of CH2, and the resulting synthase activity was expected to result in expression of a TEAS-specific product (i.e., 5-epi-aristolochene). Immunodetection assays revealed that synthase protein produced upon expression of CH7 was found to be of the correct size and expected abundance (data not shown); however, no enzyme activity was detected. The lack of enzyme activity indicated that interactions between the carboxy and amino terminal portions of the protein contributed to enzyme activity. This interpretation is further supported by comparing the specific activity of the enzymes generated by the expression of the CH5 and CH6 constructs. CH5 resulted in the expression of a product having a 10-fold lower specific activity of synthase enzyme activity than the other chimeric synthases, even though the absolute level of expressed protein was similar to the other constructs (as determined by immunodetection, data not shown). Substituting an HVS carboxy-terminal region was found to restore the specific activity to the synthase enzyme that was generated by CH6.

Comparison of CH2 and CH3 chimeric synthases provided evidence for specificity of end-product formation residing within a domain of approximately 181 amino acids, corresponding to the NdeI and ClaI restriction sites within the TEAS and HVS genes. Expression of CH4 unexpectedly resulted in the production of a chimeric synthase protein capable of generating reaction products reflective of both the TEAS and HVS enzymes. We interpreted this result to indicate that amino acids 261 to 379 within the tobacco 5-epi-aristolochene synthase are responsible for the TEAS-specific products (i.e., the region corresponding to the NdeI to HincII fragment of the cDNA), while amino acids 379 to 442 within the Hyoscyamus protein are responsible for the HVS-specific products (i.e., the region corresponding to the HincII to ClaI fragment of the cDNA).

Our interpretation was confirmed by evaluating the expression products of CH11 and CH12. CH11 represented the substitution of the NdeI to HincII fragment of the Hyoscyamus gene with the corresponding tobacco gene fragment, and resulted in the production of an enzyme having HVS- and TEAS-specificity. CH12 represented a substitution of the HincII to ClaI fragment of the tobacco gene with the corresponding Hyoscyamus gene fragment, and resulted in the production of an enzyme having HVS- and TEAS-specificity. Comparing CH11 to CH13 provided a further refinement in the domain characterization of the tobacco enzyme responsible for the TEAS-specific products. The fact that CH13 was found to be a multifunctional enzyme indicated that the 81 amino acids encoded by the DNA fragment residing between the NdeI to XbaI restriction sites of the tobacco cDNA were sufficient for formation of the predominant TEAS specific products. This interpretation was confirmed by substituting the domain contained within the NdeI/XbaI HVS cDNA restriction fragment of CH14 with that of the TEAS gene (FIG. 4A).

As shown in FIG. 4B, the predominant reaction product(s) of the wildtype tobacco TEAS and Hyoscyamus HVS genes expressed in bacteria migrated on silver nitrate-TLC plates with $R_f$ values of 0.41 and 0.31, values consistent with previous characterization of these products as 5-epi-aristolochene and vetispiradiene, respectively (Back and Chappell, *J. Biol. Chem.* 270:7375, 1995; Back et al., *Arch. Biochem. Biophys.* 315:527, 1994). GC and GC-MS analyses indicated that the predominant TEAS reaction products were 5-epi-aristolochene (70% of total products, based on percentage of total peak areas from GC analysis) and a bicyclic sesquiterpene (20%) ($[M]^+$ ion at m/z of 204). The predominant HVS reaction product was vetispiradiene (>90%) ($[M]^+$ ion at m/z of 204 with a base peak at m/z 41 and a series of predictable ions at m/z 175, 108, 94, and 68), and the predominant reaction products of CH4 were 5-epi-aristolochene (18%), a bicyclic sesquiterpene (43%), and vetispiradiene (32%) (data not shown).

In addition, studies relying on affinity purification of histidine-tagged recombinant synthase proteins has revealed 5 other minor reaction products, each representing approximately 1% of the total products, with all 5 found at the same relative abundance in all the reaction assays.

Ratio-Determinant Domain

Another domain of the synthase proteins was identified by comparing the relative ratio of the predominant reaction products produced by the multifunctional chimeric synthase enzymes (FIG. 4A). For example, the reaction products resulting from expression of constructs CH4, CH10, CH11, and CH12 were generated in a ratio of 60–70% TEAS-specific to 30–40% HVS-specific. In contrast, an inverse ratio of reaction products resulted from expression of constructs CH13 and CH14. This result indicated that the region encompassed by the XbaI to HincII domain influenced the relative ratio of reaction products generated by the multi-functional chimeric synthase enzymes. These results indicated that two separate and distinct domains within the synthase peptide contributed directly to the types of reaction products generated, and are interrupted by another domain which we refer to as the ratio-determinant domain (FIG. 5).

Site-Directed Mutagenesis

Additional analysis of the product specificity and ratio determinant domains was determined using conventional site-directed mutagenesis methodologies. The results of this analysis are presented in Table I (below). For example, the DDXXD motif, found within the aristolochene specific domain, is a conserved sequence that is found in a variety of terpene biosynthetic enzymes including TEAS and HVS. This acidic amino acid cluster is said to coordinate a metal cofactor that is necessary to neutralize the diphosphate moiety of FPP in an otherwise lipophilic pocket. Substitution of the first aspartic acid residue (D301) of the DDXXD motif with either glutamic acid (overall charge conservation) or valine (net loss of acidic charge) residues (i.e., D301→E and D301→V) resulted in the formation of an inactivated enzyme. A conserved substitution of the second aspartic acid (D302) with a glutamic acid residue (i.e., D302→E) also inactivated chimeric synthase enzyme activity by 95%, and resulted in a slight alteration of the product distribution of the multifunctional enzyme.

corresponding active domain of CH3, as outlined in FIG. 6. CH3 contains an inactive domain corresponding to exon 6 of TEAS, has convenient NdeI and XbaI restriction sites for the desired substitution, and can be overexpressed in bacteria to high levels. Domain switching is accomplished using standard molecular techniques, as described herein. In one particular example, a PCR amplification product of HVS cDNA corresponding to exon 4, encompassing amino acids 261 to 342 and containing appropriate NdeI and XbaI sites within the primers, is substituted for the corresponding region of CH3. In generating such constructs, care is exercised to maintain appropriate amino acid residues and the correct reading frame, and expression testing of the construct entails a measurement of the protein level in the soluble and insoluble fractions of bacterial lysates by immunoblotting techniques, as well as by enzyme assays.

In addition, large scale enzyme reactions are performed, the reaction product(s) are extracted into hexane, and the

TABLE I

| Mutation | Mutated | Product ratio | | Specific Activity |
|---|---|---|---|---|
| target gene | amino acid | Aristolochene | Vetispiradiene | (nmol/mg $h^{-1}$) |
| CH4 | | 66% | 34% | 34 |
| Substrate binding domain (NdeI/XbaI region) | | | | |
| Tobacco | D301V | No activity | | 0 |
| CH4 | R287A | No activity | | 0 |
| CH4 | D301V | No activity | | 0 |
| CH4 | D301E | No activity | | 0 |
| CH4 | D302E | 51% | 49% | 1.8 |
| Ratio determinant domain (XbaI/HincII region) | | | | |
| CH4 | K347I | 64% | 36% | 32 |
| CH4 | H360S | 63% | 32% | 29 |
| CH4 | H364S | 65% | 35% | 38 |
| Hyoscyamus specific domain (HincII/ClaI region) | | | | |
| CH4 | T408A | 67% | 33% | 48 |
| CH4 | K420M | 68% | 32% | 29 |
| CH4 | H422A | 67% | 33% | 30 |
| CH4 | N436S | 70% | 30% | 32 |
| CH4 | AT437, 438VI | 61% | 39% | 33 |

The sites for directed substitutions within the ratio-determinant domain (i.e., K347→I, H360→S, H364→S) were inferred by an analysis of reports that hypothesized the importance of charged amino acid residues (e.g., histidine or lysine) in synthase enzymology, and these sites represented those amino acids which displayed the greatest charge differences in comparisons between the TEAS and HVS primary sequences. None of the three mutations analyzed had any effect on overall catalytic activity or the ratio of products formed.

Amino acid substitutions within the HVS specific domain were chosen on the basis of comparisons between secondary structural predictions of the HVS and TEAS proteins. Those amino acids mutated appeared to contribute disproportionately to structural distortions in the secondary structure models of these two proteins, largely because of charge considerations. However, as shown in Table I (above), substitutions involving charged to non-charged (i.e., T408→A, K420→M, H422→A) or reduced charged (N436→S, A437→T, V438→I) amino acids did not affect overall enzyme activity, nor the synthesis rate of one product or the other.

Quiescent Synthases

To generate a quiescent synthase, the inactive domain corresponding to exon 4 of HVS is substituted with the products are purified by HPLC methods. Additional evaluation of the quiescent enzyme reaction products is carried out using TLC, and comparing the $R_f$ values of the experimental sample to those generated by the TEAS and HVS enzymes. Retention times of the reaction products (e.g., germacrene or germacrene-like reaction product) are also monitored using GC, GC-MS, and NMR according to standard methods.

The quiescent synthase is useful for providing sufficient amounts of the germacrene reaction intermediate(s) (or derivatives thereof) to confirming the chemical rationalization for the EAS and VS reactions, and produces a template chimeric synthase that may be used for the introduction of novel terminal steps in the overall synthase reaction scheme.

Chimeric Casbene and Cadinene Synthases

Chimeric isoprenoid synthases are also useful for generating novel macrocyclic isoprenoids or isoprenoids having altered stereochemical properties. For example, isoprenoid synthases such as casbene synthase, a diterpene synthase which catalyzes the synthesis of a macrocyclic diterpene harboring a cyclopropyl side group, and cadiene synthase, a sesquiterpene synthase that catalyzes the synthesis of a bicyclic sesquiterpene, provide domains useful for engineering enzymes capable of producing macrocylic isoprenoids or isoprenoid reaction products having altered sterochemical properties. A general scheme for producing such chimeric synthases is presented in FIGS. 7 and 8.

To construct such chimeric casbene and cadienne synthases, quiescent amino terminal domains (and other synthase domains as necessary) are substituted with those from casbene and cadinene synthase using convenient restriction sites and PCR amplification of selected regions as described above. Sequences corresponding to the N-terminal, plastid targeting sequence of the casbene synthase are deleted in these constructs. Chimeric constructs are expressed in bacteria, bacterial lysates are examined for chimeric synthase activity, and reaction products are characterized as described above, for example, using argentation-TLC. Constructs supporting high levels of synthase activity in bacteria and/or activity generating reaction products which migrate with Rηs different from aristolochene and vetispiradiene standards are considered useful in the invention. Reaction products are also analyzed for their retention times by GC and subjected to GC-MS and NMR, as necessary. Those domains of casbene synthase and cadinene synthase which contribute to the synthesis of unique reaction products may also be subjected to fine detail mapping using a strategy analogous to that depicted in FIG. 4A.

Production of Other Chimeric Isoprenoid Synthases

Using the standard molecular techniques described herein, other chimeric synthases may be readily generated which include domains from known or newly isolated synthase enzymes. Such chimeric synthases may be tested for activity using, for example, any appropriate enzyme assays known to those in the art, or by standard immunodetection techniques.

The isolation of additional synthase coding sequences is also possible using standard cloning strategies and techniques that are well known in the art. For example, using all or a portion of the amino acid sequence of a known synthase polypeptide, one may readily design synthase-specific oligonucleotide probes, including synthase degenerate oligonucleotide probes (i.e., a mixture of all possible coding sequences for a given amino acid sequence). These oligonucleotides may be based upon the sequence of either DNA strand and any appropriate portion of synthase nucleotide sequence. General methods for designing and preparing such probes are provided, for example, in Ausubel et al., 1996, *Current Protocols in Molecular Biology,* Wiley Interscience, New York, and Berger and Kimmel, *Guide to Molecular Cloning Techniques,* 1987, Academic Press, New York. These oligonucleotides are useful for synthase gene isolation, either through their use as probes capable of hybridizing to a synthase complementary sequences or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); Chen at al. *Arch. Biochem. Biophys.* 324:255, 1995; and Sambrook et al., *Molecular Cloning: A Laboratory Manual,* Cold Spring Harbor Laboratory Press, New York. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

As discussed above, synthase oligonucleotides may also be used as primers in amplification cloning strategies, for example, using PCR. PCR methods are well known in the art and are described, for example, in *PCR Technology,* Erlich, ed., Stockton Press, London, 1989; *PCR Protocols: A Guide to Methods and Applications,* Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, a synthase gene may be isolated using the PCR "RACE" technique, or Rapid Amplification of cDNA Ends (see, e.g., Innis et al. (supra)). By this method, oligonucleotide primers based on a synthase sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85:8998, (1988).

Useful synthase sequences may be isolated from any appropriate organism. Confirmation of a sequence's relatedness to the synthase polypeptide family may be accomplished by a variety of conventional methods, for example, sequence comparison. In addition, the activity of any synthase protein may be evaluated according to any of the techniques described herein.

Chimeric Isoprenoid Synthase Polypeptide Expression

Chimeric synthase polypeptides may be produced by transformation of a suitable host cell with all or part of a chimeric synthase DNA (for example, the chimeric synthase cDNAs described above) in a suitable expression vehicle or with a plasmid construct engineered for increasing the expression of a chimeric synthase polypeptide in vivo.

Those skilled in the field of molecular biology will appreciate that any of a wide variety of expression systems may be used to provide the recombinant protein. The precise host cell used is not critical to the invention. The chimeric synthase protein may be produced in a prokaryotic host, for example, *E. coli* TB1, or in a eukaryotic host, for example, *Saccharomyces cerevisiae,* mammalian cells (for example, COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include, but are not limited to, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Maize, Millet, Onion, Barley, Orchard grass, Oat, Rye, and Wheat.

Such cells are available from a wide range of sources including: the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., *Cell Culture and Somatic Cell Genetics of Plants,* Vol I, II, III Laboratory Procedures and Their Applications Academic Press, New York, 1984; Dixon, R. A., *Plant Cell Culture—A Practical Approach,* IRL Press, Oxford University, 1985; Green et al., *Plant Tissue and Cell Culture,* Academic Press, New York, 1987; and Gasser and Fraley, *Science* 244:1293, (1989).

For prokaryotic expression, DNA encoding a chimeric synthase polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli;* however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac), the tryptophan (Trp) (Goeddel et al., *Nucl. Acids Res.* 8:4057 (1980)), and the tac promoter systems, as well as the lambda-derived $P_L$ promoter and N-gene ribosome binding site (Simatake et al., *Nature* 292:128 (1981)).

One particular bacterial expression system for chimeric synthase polypeptide production is the *E. coli* pET expression system (Novagen). According to this expression system, DNA encoding a chimeric synthase polypeptide is inserted into a pET vector in an orientation designed to allow expression. Since the chimeric synthase gene is under the control of the T7 regulatory signals, expression of chimeric synthase is induced by inducing the expression of T7 RNA polymerase in the host cell. This is typically achieved using host strains which express T7 RNA polymerase in response to IPTG induction. Once produced, recombinant chimeric synthase polypeptide is then isolated according to standard methods known in the art, for example, those described herein.

Another bacterial expression system for chimeric synthase polypeptide production is the pGEX expression system (Pharmacia). This system employs a GST gene fusion system that is designed for high-level expression of a gene or gene fragment as a fusion protein with rapid purification and recovery of the functional gene product. The chimeric synthase protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

For eukaryotic expression, the method of transformation or transfection and the choice of vehicle for expression of the chimeric synthase polypeptide will depend on the host system selected. Transformation and transfection methods of numerous organisms, for example, the baker's yeast *Saccharomyces cerevisiae,* are described, e.g., in Ausubel et al. (supra); Weissbach and Weissbach, *Methods for Plant Molecular Biology,* Academic Press, 1989; Gelvin et al., *Plant Molecular Biology Manual,* Kluwer Academic Publishers, 1990; Kindle, K., *Proc. Natl. Acad. Sci. U.S.A.* 87:1228 (1990); Potrykus, I., *Annu. Rev. Plant Physiol. Plant Mol. Biology* 42:205 (1991); and BioRad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred eukaryotic expression system is the mouse 3T3 fibroblast host cell transfected with a pMAMneo expression vector (Clontech). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a chimeric synthase polypeptide is inserted into the pMAMneo vector in an orientation designed to allow expression. The recombinant chimeric synthase polypeptide is then isolated as described below. Other preferable host cells which may be used in conjunction with the pMAMneo expression vehicle include COS cells and CHO cells (ATCC Accession Nos. CRL 1650 and CCL 61, respectively).

Alternatively, if desired, a chimeric synthase polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the chimeric synthase polypeptide is cloned into an expression vector which includes the dihydrofolate reductase (DHFR) gene. Integration of the plasmid and, therefore, the chimeric synthase-encoding gene into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHrF and pAdD26SV(A) (described in Ausubel et al., supra). Any of the host cells described above or, preferably, a DHFR-deficient CHO cell line (for example, CHO DHFR cells, ATCC Accession No. CRL 9096) are among the host cells preferred for DHFR selection of a stably-transfected cell line or DHFR-mediated gene amplification.

A chimeric synthase polypeptide is preferably produced by a stably-transfected plant cell line or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned chimeric synthase gene under the transcriptional control of 5' and 3' regulatory sequences and (2) a dominant selectable marker. Such plant expression vectors may also contain, if desired, a promoter regulatory region (for example, one conferring inducible or constitutive expression, or environmentally- or developmentally-regulated, or pathogen- or wound-inducible, or cell- or tissue-specific expression), a transcription initiation start site, a ribosome binding site, an RNA processing signal, a transcription termination site, and/or a polyadenylation signal.

The chimeric synthase DNA sequence of the invention may, if desired, be combined with other DNA sequences in a variety of ways. The chimeric synthase DNA sequence of the invention may be employed with all or part of the gene sequences normally associated with a synthase protein. In its component parts, a DNA sequence encoding a chimeric synthase protein is combined in a DNA construct having a transcription initiation control region capable of promoting transcription and translation in a host cell.

In general, the constructs will involve regulatory regions functional in plants which provide for production of a chimeric synthase protein as discussed herein. The open reading frame coding for the chimeric synthase protein or functional fragment thereof will be joined at its 5' end to a transcription initiation regulatory region such as the sequence naturally found in the 5' upstream region of a synthase structural gene. Numerous other transcription initiation regions are available which provide for constitutive or inducible regulation.

For applications when developmental, cell, tissue, hormonal, environmental, or pathogen-inducible expression are desired, appropriate 5' upstream non-coding regions are obtained from other genes; for example, from genes regulated during seed development, embryo development, leaf development, or in response to a pathogen.

Regulatory transcript termination regions may also be provided in DNA constructs of this invention as well. Transcript termination regions may be provided by the DNA sequence encoding a synthase protein or any convenient transcription termination region derived from a different gene source. The transcript termination region will contain preferably at least 1–3 kb of sequence 3' to the structural gene from which the termination region is derived. Such genetically-engineered plants are useful for a variety of industrial and agricultural applications as discussed below. Importantly, this invention is applicable to gymnosperms and angiosperms, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313:810 (1985)). The CaMV promoter is also highly active in monocots (see, e.g., Dekeyser et al., *Plant Cell* 2:591 (1990); Terada and Shimamoto, *Mol. Gen. Genet.* 220:389, (1990)). Moreover, activity of this promoter can be further increased (i.e., between 2–10 fold) by duplication of the CaMV 35S promoter (see e.g., Kay et al., *Science* 236:1299 (1987); Ow et al., *Proc. Natl. Acad. Sci. U.S.A.* 84:4870 (1987); and Fang et al., *Plant Cell* 1:141 (1989)).

Other useful plant promoters include, without limitation, the nopaline synthase promoter (An et al., *Plant Physiol.* 88:547 (1988)) and the octopine synthase promoter (Fromm et al., *Plant Cell* 1:977 (1989)).

For certain applications, it may be desirable to produce the chimeric synthase gene product in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88:965 (1988); Takahashi and Komeda, *Mol. Gen. Genet.* 219:365 (1989); and Takahashi et al. *Plant J.* 2:751(1992)), light-regulated gene expression (e.g., the pea rbcS-3A described by Kuhlemeier et al. (*Plant Cell* 1:471 (1989); the maize rbcS promoter described by Schäffner and Sheen, (*Plant Cell* 3:997 (1991); or the chlorophyll a/b-binding protein gene found in pea described by Simpson et al. (*EMBO J.* 4:2723 (1985)), hormone-regulated gene expression (for example, the abscisic acid (ABA) responsive sequences from the Em gene of wheat described by Marcotte et al. (*Plant Cell* 1:969 (1989); the ABA-inducible HVA1 and HVA22, and the rd29A promoters described for barley and Arabidopsis by Straub et al. (*Plant Cell* 6:617 (1994), Shen et al. (*Plant Cell* 7:295 (1994)), and wound-induced gene expression (for example, of wunI described by Siebertz et al. (*Plant Cell* 1:961 (1989)), or organ-specific gene expression (for example, of the tuber-specific storage protein gene described by Roshal et al. (*EMBO J.* 6:1155 (1987); the 23-kDa zein gene from maize described by Schernthaner et al. (*EMBO J.* 7:1249 (1988); or the French bean β-phaseolin gene described by Bustos et al. (*Plant Cell* 1:839 (1989)); and pathogen-inducible gene expression described by Chappell et al. in U.S. Ser. Nos. 08/471,983, 08/443,639, and 08/577,483, hereby incorporated by reference.

Plant expression vectors may also optionally include RNA processing signals, for example, introns, which have been shown to be important for efficient RNA synthesis and accumulation (Callis et al., *Genes and Dev.* 1:1183 (1987)). The location of the RNA splice sequences can dramatically influence the level of transgene expression in plants. In view of this fact, an intron may be positioned upstream or downstream of a chimeric synthase polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84:744 (1987); An et al., *Plant Cell* 1:115 (1989)). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Alternatively, the green-fluorescent protein from the jellyfish *Aequorea victoria* may be used as a selectable marker (Sheen et al., *Plant J.* 8:777, 1995; Chiu et al., *Current Biology* 6:325 (1996)). Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller In: *Genetic Engineering,* vol 6, PWJ Rigby, ed, London, Academic Press, 1987; and Lichtenstein, C. P., and Draper, J,. In: *DNA Cloning,* Vol II, D. M. Glover, ed, Oxford, IRI Press, 1985)), (2) the particle delivery system (see, e.g., Gordon-Kamm et al., *Plant Cell* 2:603 (1990); or BioRad Technical Bulletin 1687, supra), (3) microinjection protocols (see, e.g., Green et al., supra), (4) polyethylene glycol (PEG) procedures (see, e.g., Draper et al., *Plant Cell Physiol.* 23:451 (1982); or e.g., Zhang and Wu, *Theor. Appl. Genet.* 76:835 (1988)), (5) liposome-mediated DNA uptake (see, e.g., Freeman et al., *Plant Cell Physiol.* 25:1353 (1984)), (6) electroporation protocols (see, e.g., Gelvin et al., supra; Dekeyser et al., supra; Fromm et al., *Nature* 319:791 (1986); Sheen, *Plant Cell* 2:1027 (1990); or Jang and Sheen *Plant Cell* 6:1665 (1994)), and (7) the vortexing method (see, e.g., Kindle supra). The method of transformation is not critical to the present invention. Any method which provides for efficient transformation may be employed. As newer methods are available to transform crops or other host cells, they may be directly applied.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli,* and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli.* This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the present invention, the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plants cells transformed with plant expression vectors can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned chimeric synthase polypeptide under the control of the EAS4 promoter and the nopaline synthase terminator and carrying a selectable marker (for example, kanamycin resistance) is transformed into Agrobacterium. Transformation of leaf discs (for example, of tobacco leaf discs), with vector-containing Agrobacterium is carried out as described by Horsch et al. (*Science* 227:1229 (1985)). Putative transformants are selected after a few weeks (for example, 3 to 5 weeks) on plant tissue culture media containing kanamycin (e.g., 100 μg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly effect the levels and the tissue and developmental patterns of transgene expression. Consequently, a number of transgenic lines are usually screened for each transgene to identify and select plants with the most appropriate expression profiles.

Transgenic lines are generally evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies to the chimeric synthase (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant chimeric synthase protein is expressed in any cell or in a transgenic plant (for example, as described above), it may be isolated, e.g., using affinity chromatography. In one example, an anti-chimeric synthase antibody (e.g., produced as described in Ausubel et al., supra, or by any standard technique) may be attached to a column and used to isolate the polypeptide. Lysis and fractionation of chimeric synthase-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, *Laboratory Techniques In Biochemistry And Molecular Biology,* eds., Work and Burdon, Elsevier, 1980).

These general techniques of polypeptide expression and purification can also be used to produce and isolate useful chimeric synthase fragments or analogs.

Use

The invention described herein is useful for a variety of agricultural, pharmaceutical, industrial, and commercial purposes. For example, the methods, DNA constructs, proteins, and transgenic organisms, including the bacteria, yeast, and plants described herein, are useful for improving isoprenoid synthesis, manufacturing, and production.

Our results presented above demonstrate that it is possible to modulate isoprenoid synthase activity by providing chimeric synthases. In this manner, various synthase reaction products may be modified, controlled, or manipulated, resulting in enhancement of production of numerous synthase reaction products, for example, the production of novel monoterpenes, diterpenes, and sesquiterpenes. Such compounds are useful as phytoalexins, insecticides, perfumes, and pharmaceuticals such as anti-bacterial and fungal agents.

A number of chimeric isoprenoid synthases may be engineered that are useful, for example, for the production of compounds having anti-fungal, anti-bacterial, anti-malarial, and anti-tumor properties. For example, for the production of chimeric synthases capable of catalyzing the production of anti-fungal isoprenoids, the C-terminal domain of casbene synthase (Mau and West, *Proc. Natl. Acad. Sci.* 91:8497, 1994) is joined to the N-terminal domain of TEAS, HVS, or CH9. To produce a chimeric synthase capable of catalyzing the production of anti-bacterial compounds, the C-terminal domain of cyclofarnesenone synthase (Habtermariam et al., *J. Nat. Prod.* 56:140, 1993) is joined to the N-terminal domain of TEAS, HVS, or CH9. Production of anti-malarial compounds is achieved using chimeric synthases having a C-terminal domain from artemisian synthase (El-Feraly et al., *J. Nat. Prod.* 52:196, 1989) and an N-terminal domain from TEAS, HVS, or CH9. Synthases capable of producing anti-tumor compounds are produced by joining the C-terminal domain of taxadiene synthase (Koepp et al., *J. Biol. Chem.* 270:8686, 1995) or helenalin synthase (Lee et al., *Science* 196: 533, 1977) with the N-terminal domain of TEAS, HVS, or CH9.

The invention is also useful for the production of chimeric synthases which are capable of generating insecticides. Such chimeric synthases are engineered by joining the C-terminal domain of cadenine synthase (Chen et al., *Arch. Biochem. Biophys.* 324: 255, 1995) to the N-terminal domain of TEAS, HVS, and CH9.

Finally, chimeric synthases are also useful for generating novel flavorings and perfumes. In one particular example, for the production of novel flavorings and aromas, a chimeric synthase is engineered by joining the C-terminal domain of limonene synthase (Colby et al., *J. Biol. Chem.* 268:23016, 1993) to the C-terminal domain of TEAS, HVS, or CH9.

All publications and patents mentioned in this specification are herein incorporated by reference to the same extent as if each individual publication or patent was specifically and individually indicated to be incorporated by reference.

Other Embodiments

From the foregoing description, one skilled in the art can easily ascertain the essential characteristics of this invention, and can make various changes and modifications of the invention to adapt it to various usages and conditions. Thus, other embodiments are also within the claims.

What is claimed is:

1. A nucleic acid molecule encoding a chimeric isoprenoid synthase polypeptide that comprises an asymmetrically positioned homologous domain and that catalyzes the production of isoprenoid reaction products that are not produced when said domain is positioned at its naturally-occurring site in an isoprenoid synthase polypeptide.

2. The nucleic acid molecule of claim 1 carried on a vector.

3. The nucleic acid molecule of claim 2, wherein said vector additionally comprises a control sequence operably linked to said nucleic acid molecule.

4. The nucleic acid molecule of claim 3, wherein said control sequence initiates transcription of said nucleic acid molecule.

5. The nucleic acid molecule of claim 3, wherein said control sequence further comprises a signal sequence that effects secretion of said chimeric isoprenoid synthase polypeptide.

6. A cell comprising the nucleic acid molecule of claim 1.

7. The cell of claim 6, wherein said cell is a yeast cell.

8. The cell of claim 6, wherein said cell is *E. coli.*

9. The cell of claim 6, wherein said cell expresses said chimeric isoprenoid synthase polypeptide.

10. The cell of claim 6, wherein said cell secretes said chimeric isoprenoid synthase polypeptide.

* * * * *

SEQUENCE LISTING

```
(1) GENERAL INFORMATION:

   (iii) NUMBER OF SEQUENCES: 6


(2) INFORMATION FOR SEQ ID NO:1:

     (i) SEQUENCE CHARACTERISTICS:
          (A) LENGTH: 30 base pairs
          (B) TYPE: nucleic acid
```

-continued (C) STRANDEDNESS: single
(D) TOPOLOGY: linear (ii) MOLECULE TYPE: DNA (oligonucleotide)

(xi) SEQUENCE DESCRIPTION: SEQ ID NO:1:

GGGATCGATG ACATAGCCAC GTATGAGGTT 30

(2) INFORMATION FOR SEQ ID NO:2:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:2:

AATACGACTC ACTATAG 17

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:3:

CGAGTCAACA TGGTTTATTG AGGGATA 27

(2) INFORMATION FOR SEQ ID NO:4:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:4:

TATTCTAGAT CTCTATGACG ATTATGAA 28

(2) INFORMATION FOR SEQ ID NO:5:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:5:

GGGAGCTCGA ATTCCATGGC CTCAGCAGCA GTTGCAAACT AT 42

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (oligonucleotide)

-continued (xi) SEQUENCE DESCRIPTION: SEQ ID NO:6:

GGGATCGATA ACTCTGCATA ATGTAGCATT 30